Figure 1:
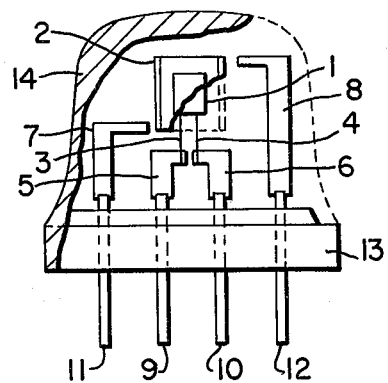

United States Patent [19]
Nakatani et al.

[11] 4,352,286
[45] Oct. 5, 1982

[54] COMBUSTIBLE GAS DETECTING ELEMENT

[75] Inventors: Yoshihiko Nakatani, Osaka; Masayuki Sakai, Katano; Seiichi Nakatani, Neyagawa; Michio Matsuoka, Ibaraki, all of Japan

[73] Assignee: Matsushita Electric Industrial Co., Ltd., Japan

[21] Appl. No.: 208,478

[22] Filed: Nov. 19, 1980

[30] Foreign Application Priority Data

Nov. 24, 1979 [JP] Japan .................. 54-152329

[51] Int. Cl.³ ............................................ G01N 27/12
[52] U.S. Cl. ........................................ 73/23; 338/34
[58] Field of Search .............. 73/23, 27 R; 338/34; 340/634; 422/98

[56] References Cited

U.S. PATENT DOCUMENTS 3,999,947 12/1976 Mihara et al. .................. 73/23
4,001,757 1/1977 Sato et al. ..................... 73/23
4,045,178 8/1977 Okinaka et al. .............. 422/98

Primary Examiner—Stephen A. Kreitman
Attorney, Agent, or Firm—Wenderoth, Lind & Ponack

[57] ABSTRACT

There is provided a novel combustible gas detecting element and method for production thereof. The element comprises a gas sensing body comprising a sintered body or film of an amorphous semiconductor comprising a metal oxide, a sulfate and halide.

7 Claims, 1 Drawing Figure

COMBUSTIBLE GAS DETECTING ELEMENT

This invention relates to a combustible gas detecting element which has superior gas response characteristics to a variety of combustible gases, and stable characteristics for a long term operation.

As a rule, the methods of detecting a combustible gas by solid materials include two methods. In one of these methods, a combustible gas is detected by the temperature rise due to its combustion on the catalyzer by means of a resistor such as a platinum wire of which electric resistance is dependent upon the temperature. In the other method of detecting a combustible gas the change in an electric resistance of a semiconductor due to the adsorption of gas thereon is detected. The former gives an output in proportion to the concentration of gas and accordingly may be used principally for a gas concentration meter and the like. The latter can provide an inexpensive detecting means and accordingly may be used as a gas leak detector and the like.

The present invention provides a gas detecting element of the semiconductor type which is useful as a combustible gas detecting means according to the latter method.

A gas sensing element is maintained in an atmosphere of high temperature because a gas sensing element of the semiconductor type requires, in general, a high speed response. Thus oxides which are stable in an oxidizing atmosphere are usually selected as gas sensing bodies.

Also, a porous sintered body or a sintered film composed of an oxide semiconductor formed on substrate is used for a gas sensing body. A crystalline substance is used in either case.

Such a detecting element composed of an oxide semiconductor usually has gas selectivity to a certain extent. When sensitivity to various kinds of combustible gases are examined, some detecting elements are found to have a particularly high sensitivity to certain kinds of gases, or a low sensitivity to other kinds of gases. The gas selectivity is very important for some purposes. On the other hand, there are some cases wherein a detecting element, capable of responding equally to all kinds of combustible gases, is required. For example, a detecting element having a strong selectivity to carbon monoxide is required, if only carbon monoxide of a small amount possessing a strong toxicity is to be selectively detected.

On the other hand when it is used for a gas leak alarm or others in home, a general purpose detecting element is required, which responds almost equally to almost equal concentrations of methane, which is a principal component of natural gas, propane, and hydrogen. If a latter detecting element which responds equally to various kinds of gases is realized, it would be possible to be used both for propane gas and natural gas: therefore the area of the application of the detecting element would be expanded.

Besides, conventional combustible gas detecting elements using metal oxide semiconductors have gas selectivity more or less. This is said to be determined by the depth of donor level or acceptor level in the semiconductor, or the amount of active adsorption points on the surface of the semiconductor. It can be thought that each energy level described above has a value almost inherent to the material, so that the semiconductor has gas selectivity.

It is an object of the present invention to realize a gas detecting element of highly general purpose for many combustible gases including methane gas, by giving a wide distribution to the material constant of these semiconductors. That is: selectivity is decreased by using an amorphous semiconductor as the detecting material, so that the gas detecting element responds equally to a variety of combustible gases.

It is said that in the solid phase of amorphous semiconductor, there are many bonds which are not related to the combination, and these bonds form the trap levels throughout a wide energy level range in a forbidden band of the semiconductor. It is also said that if these levels are filled with various kinds of impurities and others, it is said that the amorphous semiconductor will become an n-type or p-type semiconductor. In this case, donor levels and acceptor levels are not at constant energy positions, but are distributed in a wide energy range. Also, the amorphous material does not have a fixed lattice constant, therefore has active adsorption points for a variety of gases.

For the reasons described above, the amorphous semiconductor, in which amorphous material is used as the detecting material, loses its sharp gas selectivity and is capable of responding to a variety of gases.

This invention will be more detailedly described hereinafter with the aid of the accompanying drawings, in which:

FIG. 1 is a perspective view of an example of a gas detecting element of this invention in the form of a sintered body.

EXAMPLE 1

Each of commercially available ferric chloride ($FeCl_3.6H_2O$) 30 g. and ferrous sulfate ($FeSO_4.7H_2O$) 60 g. were dissolved in 1 liter of water and stirred with temperature kept at 10° C. Also, with the temperature being kept at 10° C., 8 N ammonium hydroxide ($NH_4OH$) was added to the solution drop by drop at a rate of 10 cc/min. until the solution was at pH 5. After the addition of ammonium hydroxide, the solution was kept at 10° C. for 10 minutes and then the copreciptate was filtered by suction. Then, the obtained powder was dried in vacuum in a reduced pressure vessel.

The dried substance was heat-treated in air at 400° C. for 1 hour and crushed for 2 hours, and then granulated by using an organic binder to obtain particles of 100 to 200 micrometers size. Two platinum wires for electrodes were embedded in the powder formed as above, and the powder was pressure-molded to form a right circular cylinder of the diameter 2 mm, height 3 mm, and sintered in air at 550° C. for 2 hours. A detecting element was made by fixing the obtained porous sintered sensing body on the base for gas detector, arranging a coil-shape heater around the sintered sensing body and covered with a net of stainless steel for explosion protection.

FIG. 1 shows a structure of a gas detecting element. Referring to FIG. 1, reference numeral 1 designates a sensing body in which two platinum wires 3 and 4 are embedded. Reference numeral 2 designates a heater for heating the sensing body, wherein the electric power is supplied from heater pins 11 and 12 through heater frames 7 and 8. The resistance of the sensing body is constructed to be measured between the pins 9 and 10 for the sensing body from the platinum electrodes 3 and 4 through the frames 5 and 6 for the sensing body. The heater pins 11, 12 and pins 9, 10 for the responsive body, are fixed to the base 13, and the stainless steel net 14 is fixed to the base.

The sensing body sintered at 550° C. does not have a particular line by X-ray diffraction, and also shows a different pattern from the pattern of α-type ferric oxide by the measurement of Mössbauer effect. It became obvious that a large amount of sulfate radical or hydroxyl group or chlorine was present. As the result of these analyses, it can be concluded that α-$Fe_2O_3$ of this sintered body does not undergo crystallization, but remains in the amorphous state.

Next, gas response characteristics were measured with respect to the detecting element which sensing body was the amorphous sintered body described above. Air was preliminarily filled in a measurement chamber with known volume, and the air was stirred slowly an continuously. The detecting element was preliminarily connected to the socket on the inner wall of the chamber, and the temperature of the sensing body was kept at 350° C. by applying an electric current to the heater. Then, gas to be tested was injected into the measurement chamber with an injector, and the resistance change of the sensing body was measured. In the case of measurement for a liquid such as alcohol, a heated substrate was put in the chamber, and the liquid was dripped onto the substrate with an injector to vaporize thereafter.

The electric resistance ($R_o$) between the two electric terminals of the sensing body heated in air at 350° C. was $7.5 \times 10^6$ Ω. Under the condition that the amount of the gas injected into the measurement chamber was 0.5 volume % and that the electric resistance of the sensing body in the injected gas was $R_G$, $(R_o - R_G)/R_o$ was measured for various kinds of gases. The result is shown in Table 1.

TABLE 1

| Name of gas | Rate of resistance change (%) |
| --- | --- |
| methane | 26.5 |
| ethyl alcohol | 23.0 |
| hydrogen | 29.1 |
| isobutane | 29.4 |
| acetone | 29.7 |

Table 1 indicates that $(R_o - R_G)/R_o$ values for the gases having the same concentrations are nearly the same. That is to say, each gas is adsorbed on the sensing body relatively evenly to cause the resistance change. This can also be understood as that the numbers of the adsorbed molecules are nearly the same, and one molecule contributes equally to the change of resistance.

In fact, in the case of a gas leak alarm, it is preferable that the gas detecting elements would operate at constant concentrations described by LEL unit, for example the alarm is constantly operated at the concentration of one tenth of lower explosion limit (LEL) concentration. But practically, the gas detecting element can be used as a detecting element for an alarm if it is made to detect a gas in certain range of concentration and to operate. Thus it can be said that the detecting element, which indicates nearly the same sensitivity but not completely the same sensitivity, to the same volume and the same concentration as shown in Table 1, is also useful.

Next, under the condition that a current was applied to the heater to keep the temperature of the sensing body at 350° C., the detecting element was simply left for 100 days in an atmosphere of ambient temperature 40° C. and relative humidity 90%, and then gas response characteristics were examined. At this time, the resistance in clean air was $6.6 \times 10^6$ Ω. Next, gas response characteristics were examined with the method previously described. The result is shown in Table 2.

TABLE 2

| Name of gas | Rate of resistance change (%) $\frac{R_o - R_G}{R_o}$ |
| --- | --- |
| methane | 25.4 |
| ethyl alcohol | 24.0 |
| hydrogen | 30.6 |
| isobutane | 30.2 |
| acetone | 29.0 |

By comparing Table 2 with Table 1, it is evident that deterioration of sensitivity is not found even after the samples were left for a long time in an atmosphere of high temperature and high humidity, that is, the detecting element has stable life characteristics.

On the other hand, a crystallized body was made by changing the conditions of production, and was compared with this example.

COMPARISON EXAMPLE 1

The starting material used was the same as that in the Example 1 above. Aqueous solution of $FeCl_3$ and $FeSO_4$ was kept at 80° C. 8 N solution of ammonium hydroxide was dripped therein at the rate of 10 cc/min. and stirred, and was stopped when the solution reached pH 10.0. After the dripping, the temperature of the solution was kept at 80° C. for 10 minutes, and the coprecipitate was filtered by suction and washed with water several times. Obtained powders were dried at 110° C., the dried substance was heat-treated in air for an hour at 400° C., crushed for two hours, and granulated to obtain particles of 100 to 200 micrometers size. The following process was the same as that in Example 1.

The sintered body, obtained by this process, was confirmed to have a peak corresponding to α-$Fe_2O_3$ in X-ray diffraction pattern, and to have a crystal phase of α-$Fe_2O_3$ by Mössbauer measurement. Also, almost no existence of hydroxyl group, sulfate radical or chlorine was confirmed as the result of chemical analysis and infra-red rays spectral analysis.

Gas responsive characteristics were examined by the same method as the case of Example 1. The result is shown in Table 3. At this time, resistance in air $R_o$ was $4.2 \times 10^6$ Ω.

TABLE 3

| Name of gas | Rate of resistance change (%) |
| --- | --- |
| methane | 3.7 |
| ethyl alcohol | 15.5 |
| hydrogen | 18.0 |
| isobutane | 28.3 |
| acetone | 20.8 |

Referring to Table 3, it can be seen that isobutane is efficiently adsorbed to the sensing body, but methane is very difficult to be adsorbed. That is to say, the sensitivity of the sensing body to methane is very low in comparison with that in Example 1. Also, when this sensing body was left at 350° C. in a high temperature and high humidity of atmosphere in which ambient temperature was 40° C. and relative humidity was 90%, for about 20 days, the response characteristics became unstable, especially the low sensitivity to methane became much lower than before.

EXAMPLE 2

Aqueous solutions using commercially available tin sulfate ($Sn(SO_4)_2.2H_2O$), indium sulfate ($In_2(SO_4)_3.9H_2O$), copper sulfate ($CuSO_4.5H_2O$) and zinc sulfate ($ZnSO_4.7H_2O$), respectively, were made, and one or at least two kinds of these aqueous solutions were added to the mixed aqueous solutions of $FeCl_3$ and $FeSO_4$ which was used for coprecipitation in Example 1, to obtain many kinds of mixed solutions. Solutions of $NH_4OH$ were dripped into these mixed solutions under the same condition as in Example 1 to obtain a precipitate, and a detecting element was produced by the same method as in Example 1, and then gas response characteristics were measured. The temperature of the sensing body in the gas detecting element was 350° C.

Table 4 shows compositions of the sensing body, the resistance $R_o$ in clean air, and $(R_o-R_G)/R_o$ for each gas at 0.5 volume % (where $R_G$ designates the resistance in the air containing a gas of 0.5 volume %).

It is evident from Table 4 that the sensitivity $(R_o-R_G)/R_o$ to each gas, of amorphous semiconductor constructed by the system of Fe—O—($SO_4$,OH,Cl), becomes high by adding Sn, In, Cu or Zn. But if the amount of added substance becomes larger than the amount of elemental iron, the sensitivity to methane becomes lower, or the resistance of some substance decreases abnormally, that is, worse results are caused. At the same time, the sensitivity deteriorates over long-term operation.

In the sintered body obtained as a gas sensing body, the existence of crystalline substance was not found as a result of X-ray diffraction, and the existence of sulfate radical, hydroxyl group and chlorine was found as a result of chemical analysis and infra-red spectral analysis. From these experiments, the sintered body is thought to be composed mainly of amorphous semiconductor, but some crystalline substance which cannot be detected by X-ray diffraction because of too small particles or too small amount of some crystalline substance may possibly to exist in the sintered body.

COMPARISON EXAMPLE 2

Aqueous solutions using commercially available tin sulfate ($Sn(SO_4)_2.2H_2O$), indium sulfate ($In_2(SO_4)_3.9H_2O$), copper sulfate ($CuSO_4.5H_2O$), and zinc sulfate ($ZnSO_4.7H_2O$), respectively, were made, and one or at least two kinds of these aqueous solutions were added to the mixed aqueous solution of $FeCl_3$ and $FeSO_4$ used for coprecipitation in Comparison Example 1, to obtain many kinds of mixed solutions. Solution of $NH_4OH$ was dripped into the mixed solutions in the same way as Comparison Example 1 to make precipitate substance. A detecting element was made by the same method as in Example 1, and then gas response characteristics were measured. The temperature of the sensing body was 350° C. Every sensing body indicated the gas response characteristics which had similar trend to the case of Comparison Example 1, especially the sensitivity to methane was low.

As the result of X-ray analysis of these sensing bodies, crystalline phases of $SnO_2$, $In_2O_3$, CuO or ZnO were found in accordance with the components of starting powder, other than the phase of $\alpha$-$Fe_2O_3$. As the result of chemical analysis and infra-red spectral analysis, sulfate radical, hydroxyl group and chlorine were proved not to be contained. Also, deterioration of characteristics in high temperature and high humidity was large similar to the case of Comparison Example 1, especially deterioration of sensitivity to methane was conspicuous.

EXAMPLE 3

Each of commercially available ferrous sulfate ($FeSO_4.7H_2O$) 60 g and iron fluoride ($FeF_3.3H_2O$) 30 g was dissolved in 1 liter of water, and then they were mixed. One or at least two kinds of aqueous solutions of $Sn(SO_4)_2.2H_2O$, $In_2(SO_4)_3.9H_2O$, $CuSO_4.5H_2O$ and $ZnSO_4.7H_2O$ were mixed, to make aqueous solutions for coprecipitation. A solution of $NH_4OH$ was dripped into these mixed solutions under the same condition as in Example 1 to obtain a precipitate, and a detecting element was made by the same method as in Example 1, and then gas response characteristics were measured. The temperature of the sensing body in the element was 400° C. Table 5 shows the relationship among the compositions of metal element of the responsive body, the resistance in clean air, and $(R_o-R_G)/R_o$ to each gas of 0.5 volume %.

It is evident from Table 5 that the sensitivity to each gas, $(R_o-R_G)/R_o$ will be increased to indicate the same trend as in Example 2, if Sn, In, Cu or Zn is added to the amorphous semiconductor composed of the system of Fe—O—($SO_4$, OH,F). The sensitivity to each combustible gas of the detecting element of this example was stable even after a long term operation in an atmosphere of high temperature and high humidity.

As a result of X-ray diffraction, no crystalline substance was found in the sintered body, and as a result of chemical analysis and infra-red spectral analysis, the existence of the sulfate radical, hydroxyl group and fluorine was found. From the foregoing, the sintered body is thought to be composed of the substance in which the main component is an amorphous semiconductor.

COMPARISON EXAMPLE 3

Each of commercially available ferrix oxide ($\alpha$-$Fe_2O_3$), cupric oxide (CuO), zinc oxide (ZnO), stannic oxide ($SnO_2$) and indium oxide ($In_2O_3$) was weighed and mixed to make 22 kinds of combinations of metal elements as shown in Table 5. Each mixture was mixed for 2 hours and was crushed. And then the obtained substances were granulated with the organic binder to the size of 100 to 200 micrometers, to obtain powder materials. By using these powders, detecting elements were made by the same method as in Example 1, and gas response characteristics of each detecting element were examined. The results are shown in Table 6.

It is evident in comparison with the results shown in Table 5 that the sensitivities are low in all, especially the sensitivity to methane is the smallest. As a result of X-ray diffraction for each sintered sensing body, $\alpha$-$Fe_2O_3$ and CuO, ZnO, $SnO_2$ or $In_2O_3$ corresponding to each component, and a little spinel phase were observed. As the result of chemical analysis and infra-red spectral analysis, the existence of hydroxyl group, sulfate radical and chlorine was not found.

In the preceding descriptions, responsive characteristics of gas detecting elements which responsive body are made of amorphous semiconductor, were explained, by using three examples and three comparison examples.

As a conclusion from these examples, it proved that the sensitivity to methane is especially low in the case of the crystallized sensing body, but that the sensitivity to any combustible gases is large, and shows extremely high stability in an atmosphere of high temperature and high humidity.

It is thought that this is partly because gas active adsorption points exist equally in various kinds of gases because of random distances between atoms in the sensing body, and partly because donor level and acceptor level are not constant in the semiconductor and have wide range of energy distribution so that the sensing element does not have selectivity to various kinds of gases which have different adsorption energy.

In general, if an amorphous substance is left at high temperature, separation of the crystalline phase will occur. The samples of the examples also proved that crystallization was caused at high temperature. But the temperature necessary to activate the sensing body of the detecting element is low enough as compared with the temperature necessary for the crystallization, so that the crystallization of the sensing body is not thought to procede if current is passes through over a long time. It is also thought that the remainder of sulfate radical in an amorphous semiconductor may protect against crystallization, to contribute to the stabilization of the sensing body.

Also, in the explanation of the Examples, the sintered body made by sintering a molded body is used as the sensing body of the detecting element, but it is possible that the material of this sintered body is made into a paste and coated on the substrate, and then burned to obtain the sensing body.

As explained above, the present invention provides a gas detecting element having also a high sensitivity to methane which was conventionally said to be difficult to be detected, at relatively low temperatures, by using amorphous semiconductor as its gas sensing body. Also, another great significance of this invention is that the high sensitivity to methane is realized without using valuable metal catalyzer which is added to many of the conventional gas detecting elements using metal-oxide semiconductors.

Also, as it is evident from the purpose of the present invention, all of the sintered body used as the sensing body need not be amorphous the gas detecting element of the purpose of the present invention can be provided even if the crystalline substance inactive to gas or a small amount of active crystalline substance is contained in the sintered body.

TABLE 4

| Mixing ratio of metal element (atom %) | | | | | $R_o$ | $(R_o - R_G)/R_o$ (%) | | | | |
|---|---|---|---|---|---|---|---|---|---|---|
| Fe | Cu | Zn | Sn | In | (MΩ) | methane | ethyl-alcohol | hydrogen | isobutane | acetone |
| 98.0 | 2.0 | — | — | — | 7.4 | 34.3 | 28.5 | 27.2 | 30.5 | 26.8 |
| 98.0 | — | 2.0 | — | — | 7.3 | 32.1 | 27.2 | 24.7 | 28.8 | 24.1 |
| 98.0 | — | — | 2.0 | — | 7.7 | 29.2 | 30.9 | 29.9 | 27.9 | 28.7 |
| 98.0 | — | — | — | 2.0 | 7.9 | 36.5 | 27.0 | 31.2 | 32.3 | 32.5 |
| 98.0 | 1.0 | 1.0 | — | — | 7.3 | 27.2 | 29.2 | 25.5 | 28.2 | 31.7 |
| 98.0 | — | 1.0 | 1.0 | — | 7.9 | 28.5 | 30.4 | 24.2 | 27.9 | 31.2 |
| 98.0 | — | — | 1.0 | 1.0 | 8.5 | 27.4 | 28.0 | 26.5 | 29.2 | 34.7 |
| 98.0 | 1.0 | — | 1.0 | — | 8.8 | 31.1 | 30.1 | 26.2 | 28.2 | 36.3 |
| 70.0 | 10.0 | 10.0 | 10.0 | — | 11.5 | 63.3 | 67.7 | 64.0 | 52.8 | 42.9 |
| 70.0 | — | 10.0 | 10.0 | 10.0 | 13.0 | 78.5 | 68.2 | 85.4 | 86.2 | 87.5 |
| 60.0 | 10.0 | 10.0 | 10.0 | 10.0 | 14.2 | 72.4 | 69.8 | 72.5 | 72.1 | 87.4 |
| 55.0 | — | 45.0 | — | — | 3.8 | 41.7 | 53.0 | 48.1 | 52.3 | 68.2 |
| 55.0 | — | — | 45.0 | — | 13.5 | 69.1 | 73.4 | 67.2 | 88.2 | 72.1 |
| 55.0 | 20.0 | — | — | 25.0 | 19.0 | 35.2 | 43.3 | 41.0 | 58.7 | 61.2 |
| 55.0 | — | 20.0 | — | 25.0 | 4.2 | 37.7 | 39.6 | 38.5 | 41.5 | 33.7 |
| 55.0 | — | — | 20.0 | 25.0 | 15.4 | 42.9 | 45.2 | 47.0 | 49.8 | 38.0 |
| 55.0 | 45.0 | — | — | — | 21.3 | 38.6 | 45.3 | 42.2 | 47.8 | 54.3 |
| 55.0 | — | — | — | 45.0 | 22.3 | 25.3 | 33.3 | 35.5 | 41.2 | 43.1 |
| 45.0 | 55.0 | — | — | — | 27.3 | 12.1 | 35.1 | 26.8 | 33.0 | 48.2 |
| 45.0 | — | 30.0 | 25.0 | — | 4.1 | 18.0 | 48.3 | 42.9 | 43.3 | 25.4 |
| 45.0 | — | 55.0 | — | — | 1.8 | 6.9 | 33.8 | 33.4 | 42.3 | 32.8 |
| 45.0 | — | — | 55.0 | — | 28.8 | 9.1 | 86.0 | 65.1 | 78.9 | 53.8 |

TABLE 5

| Mixing ratio of metal element (atom %) | | | | | $R_o$ | $(R_o - R_G)/R_o$ (%) | | | | |
|---|---|---|---|---|---|---|---|---|---|---|
| Fe | Cu | Zn | Sn | In | (MΩ) | methane | ethyl-alcohol | hydrogen | isobutane | acetone |
| 98.0 | 2.0 | — | — | — | 5.4 | 31.3 | 29.4 | 28.7 | 32.5 | 27.0 |
| 98.0 | — | 2.0 | — | — | 5.0 | 29.5 | 28.1 | 25.2 | 30.1 | 25.2 |
| 98.0 | — | — | 2.0 | — | 5.7 | 28.8 | 32.3 | 31.5 | 29.2 | 30.1 |
| 98.0 | — | — | — | 2.0 | 5.9 | 30.2 | 28.3 | 29.2 | 33.2 | 34.2 |
| 98.0 | 1.0 | 1.0 | — | — | 4.9 | 25.3 | 30.2 | 28.3 | 29.5 | 32.4 |
| 98.0 | — | 1.0 | 1.0 | — | 5.2 | 24.8 | 31.5 | 25.4 | 29.5 | 32.4 |
| 98.0 | — | — | 1.0 | 1.0 | 6.3 | 26.5 | 29.8 | 27.3 | 29.4 | 33.5 |
| 98.0 | 1.0 | — | 1.0 | — | 6.4 | 28.0 | 27.5 | 26.2 | 28.2 | 34.0 |
| 70.0 | 10.0 | 10.0 | 10.0 | — | 8.4 | 57.5 | 68.5 | 65.0 | 51.5 | 43.2 |
| 70.0 | — | 10.0 | 10.0 | 10.0 | 9.7 | 60.5 | 68.9 | 85.3 | 85.2 | 87.5 |
| 60.0 | 10.0 | 10.0 | 10.0 | 10.0 | 10.2 | 66.2 | 70.5 | 75.0 | 73.3 | 86.5 |
| 55.0 | — | 45.0 | — | — | 2.7 | 40.5 | 52.1 | 42.3 | 48.1 | 64.3 |
| 55.0 | — | — | 45.0 | — | 10.5 | 67.5 | 74.2 | 67.3 | 85.2 | 69.4 |
| 55.0 | 20.0 | — | — | 25.0 | 15.3 | 33.1 | 43.9 | 44.0 | 58.8 | 61.1 |
| 55.0 | — | 20.0 | — | 25.0 | 3.0 | 32.4 | 40.8 | 37.4 | 40.3 | 34.5 |
| 55.0 | — | — | 20.0 | 25.0 | 12.4 | 37.5 | 47.2 | 47.1 | 52.0 | 37.5 |
| 55.0 | 45.0 | — | — | — | 15.4 | 38.4 | 45.3 | 42.8 | 49.6 | 51.2 |

TABLE 5-continued

| Mixing ratio of metal element (atom %) | | | | | $R_o$ | $(R_o - R_G)/R_o$ (%) | | | | |
|---|---|---|---|---|---|---|---|---|---|---|
| Fe | Cu | Zn | Sn | In | (MΩ) | methane | ethyl-alcohol | hydrogen | isobutane | acetone |
| 55.0 | — | — | — | 45.0 | 15.9 | 35.2 | 34.2 | 38.4 | 40.5 | 42.0 |
| 45.0 | 55.0 | — | — | — | 19.8 | 25.3 | 33.1 | 27.1 | 35.1 | 45.0 |
| 45.0 | — | 30.0 | 25.0 | — | 3.2 | 11.3 | 47.5 | 43.8 | 41.1 | 25.4 |
| 45.0 | — | 55.0 | — | — | 1.1 | 5.4 | 31.5 | 29.2 | 43.0 | 33.4 |
| 45.0 | — | — | 55.0 | — | 20.2 | 8.7 | 85.3 | 65.2 | 75.4 | 52.8 |

TABLE 6

| Mixing ratio of metal element (atom %) | | | | | $R_o$ | $(R_o - R_G)/R_o$ (%) | | | | |
|---|---|---|---|---|---|---|---|---|---|---|
| Fe | Cu | Zn | Sn | In | (MΩ) | methane | ethyl-alcohol | hydrogen | isobutane | acetone |
| 98.0 | 2.0 | — | — | — | 2.6 | 1.1 | 1.2 | 1.8 | 1.9 | 1.6 |
| 98.0 | — | 2.0 | — | — | 2.1 | 1.2 | 2.1 | 2.4 | 1.9 | |
| 98.0 | — | — | 2.0 | — | 2.7 | 1.4 | 1.5 | 4.8 | 5.0 | 3.2 |
| 98.0 | — | — | — | 2.0 | 2.8 | 1.2 | 1.3 | 2.4 | 3.1 | 2.1 |
| 98.0 | 1.0 | 1.0 | — | — | 2.2 | 1.2 | 1.3 | 3.0 | 3.6 | 2.1 |
| 98.0 | — | 1.0 | 1.0 | — | 2.6 | 1.5 | 1.5 | 5.6 | 6.1 | 3.6 |
| 98.0 | — | — | 1.0 | 1.0 | 3.0 | 1.4 | 1.6 | 5.3 | 6.0 | 2.1 |
| 98.0 | 1.0 | — | 1.0 | — | 2.8 | 1.2 | 1.3 | 4.0 | 5.4 | 1.4 |
| 70.0 | 10.0 | 10.0 | 10.0 | — | 1.7 | 2.5 | 4.7 | 11.1 | 16.5 | 6.1 |
| 70.0 | — | 10.0 | 10.0 | 10.0 | 1.4 | 2.5 | 4.6 | 12.1 | 14.9 | 6.4 |
| 60.0 | 10.0 | 10.0 | 10.0 | 10.0 | 2.7 | 2.5 | 6.8 | 20.5 | 27.7 | 9.9 |
| 55.0 | — | 45.0 | — | — | 0.7 | 3.4 | 4.8 | 8.8 | 10.0 | 4.9 |
| 55.0 | — | — | 45.0 | — | 1.6 | 4.8 | 13.6 | 21.4 | 29.5 | 13.7 |
| 55.0 | 20.0 | — | — | 25.0 | 4.7 | 1.2 | 1.2 | 7.2 | 8.4 | 2.6 |
| 55.0 | — | 20.0 | — | 25.0 | 1.9 | 1.7 | 1.9 | 9.8 | 13.5 | 2.5 |
| 55.0 | — | — | 20.0 | 25.0 | 3.6 | 3.8 | 3.3 | 12.3 | 19.8 | 6.7 |
| 55.0 | 45.0 | — | — | — | 5.4 | 1.2 | 1.3 | 2.3 | 3.3 | 2.1 |
| 55.0 | — | — | — | 45.0 | 4.8 | 1.3 | 1.5 | 7.7 | 8.8 | 1.8 |
| 45.0 | 55.0 | — | — | — | 8.6 | 1.3 | 1.5 | 6.2 | 7.9 | 2.9 |
| 45.0 | — | 30.0 | 25.0 | — | 2.1 | 3.9 | 15.9 | 20.0 | 30.1 | 17.7 |
| 45.0 | — | 55.0 | — | — | 0.8 | 2.2 | 3.1 | 10.1 | 17.1 | 4.5 |
| 45.0 | — | — | 55.0 | — | 7.4 | 5.1 | 17.6 | 29.8 | 32.5 | 17.6 |

What is claimed is:

1. A combustible gas detecting element comprising a gas sensing body comprising a sintered body or film of an amorphous semiconductor comprising a metal oxide, a sulfate and halide.

2. The combustible gas detecting element according to claim 1, wherein said metal oxide is mainly composed of iron.

3. The combustible gas detecting element according to claim 1, wherein said metal element is composed of at least 50 percent of iron and the remainder of at least one compound selected from the group consisting of copper, zinc, tin and indium.

4. The combustible gas detecting element according to claim 1, further including a hydroxyl group.

5. The combustible gas detecting element according to claim 1 wherein said halide is chloride or fluoride.

6. The combustible gas detecting element according to claim 1 wherein said amorphous semiconductor comprises Fe—O—($SO_4$, OH, Cl) or Fe—O—($SO_4$, OH, F).

7. The combustible gas detecting element according to claim 6 which further includes at least one compound selected from the group consisting of copper, indium, tin an zinc.

* * * * *